(12) United States Patent
Chae et al.

(10) Patent No.: US 11,872,048 B2
(45) Date of Patent: Jan. 16, 2024

(54) ELECTROCARDIOGRAM MEASUREMENT SYSTEM COMPRISING PATCH-TYPE ELECTROCARDIOGRAM MEASUREMENT APPARATUS

(71) Applicant: ATSENS CO., LTD., Gyeonggi-do (KR)

(72) Inventors: Deok Byeong Chae, Gyeonggi-do (KR); Chang Ho Lee, Gyeonggi-do (KR); Jong Sung Kim, Gyeonggi-do (KR); Jong Ook Jeong, Gyeonggi-do (KR)

(73) Assignee: ATSENS CO., LTD., Gyeonggi-do (KR)

( * ) Notice: Subject to any disclaimer, the term of this patent is extended or adjusted under 35 U.S.C. 154(b) by 0 days.

(21) Appl. No.: 16/998,401

(22) Filed: Aug. 20, 2020

(65) Prior Publication Data
US 2020/0375488 A1 Dec. 3, 2020

Related U.S. Application Data

(63) Continuation of application No. PCT/KR2019/000906, filed on Jan. 22, 2019.

(30) Foreign Application Priority Data

Feb. 22, 2018 (KR) ........................ 10-2018-0021064

(51) Int. Cl.
*A61B 5/339* (2021.01)
*A61B 5/00* (2006.01)
*A61B 5/333* (2021.01)

(52) U.S. Cl.
CPC ............ *A61B 5/339* (2021.01); *A61B 5/0006* (2013.01); *A61B 5/333* (2021.01); *A61B 5/6833* (2013.01); *A61B 5/746* (2013.01)

(58) Field of Classification Search
CPC ..... A61B 5/044; A61B 5/0006; A61B 5/0432; A61B 5/6833; A61B 5/746; A61B 5/00; A61B 5/0408

(Continued)

(56) References Cited

U.S. PATENT DOCUMENTS 3,759,248 A * 9/1973 Valiquette ............ A61B 5/0436
600/516
4,250,888 A * 2/1981 Grosskopf ........... A61B 5/0245
600/515

(Continued)

FOREIGN PATENT DOCUMENTS

JP 2006-520657 9/2006
JP 2011-514831 5/2011

(Continued)

OTHER PUBLICATIONS

International Search Report for International Application PCT/KR2019/000906, dated May 7, 2019.

(Continued)

*Primary Examiner* — Jacqueline Cheng
*Assistant Examiner* — Tho Q Tran
(74) *Attorney, Agent, or Firm* — Guntin & Gust, PLC

(57) ABSTRACT

An electrocardiogram measurement system includes a patch-type electrocardiogram measurement apparatus; a first device connected to the electrocardiogram measurement apparatus by means of a first communication and configured to store electrocardiogram data measured by the electrocardiogram measurement apparatus; and a second device connected to the electrocardiogram measurement apparatus by means of the first communication and configured to store electrocardiogram data measured by the electrocardiogram measurement apparatus. The electrocardiogram data mea- (Continued)

sured by the electrocardiogram measurement apparatus includes measured time information.

11 Claims, 5 Drawing Sheets

(58) Field of Classification Search
USPC .......................................................... 600/481
See application file for complete search history.

(56) References Cited

U.S. PATENT DOCUMENTS

| | | | |
|---|---|---|---|
| 6,441,747 | B1 | 8/2002 | Khair et al. |
| 6,671,705 | B1 * | 12/2003 | Duprey ............... G06F 11/2082 |
| 7,515,043 | B2 | 4/2009 | Welch et al. |
| 10,258,282 | B2 | 4/2019 | Huppert et al. |
| 10,349,457 | B1 * | 7/2019 | Oh ....................... H04W 76/14 |
| 10,394,835 | B1 * | 8/2019 | Rickrode ............ G06F 21/604 |
| 2002/0101711 | A1 * | 8/2002 | Gold ............................ 361/685 |
| 2003/0060689 | A1 * | 3/2003 | Kohls .................. A61B 5/0002 |
| | | | 600/300 |
| 2003/0163655 | A1 * | 8/2003 | McKean ............ G06F 12/0815 |
| | | | 711/141 |
| 2005/0113703 | A1 * | 5/2005 | Farringdon .......... A61B 5/0205 |
| | | | 600/509 |
| 2007/0198722 | A1 * | 8/2007 | Kottomtharayil ....... H04L 47/70 |
| | | | 709/226 |
| 2008/0215546 | A1 * | 9/2008 | Baum ................. G06F 16/2322 |
| 2009/0019090 | A1 * | 1/2009 | Donnelly, III ..... G11B 20/1803 |
| 2010/0125682 | A1 * | 5/2010 | Andres ............... G06F 11/2092 |
| | | | 710/15 |
| 2012/0099913 | A1 * | 4/2012 | Joseph ................. B41J 11/0075 |
| | | | 400/582 |
| 2012/0156933 | A1 * | 6/2012 | Kreger ............... A61B 5/14552 |
| | | | 439/625 |
| 2013/0317377 | A1 * | 11/2013 | Gupta .................. A61B 5/0024 |
| | | | 600/515 |
| 2014/0275898 | A1 | 9/2014 | Taub et al. |
| 2014/0330091 | A1 | 11/2014 | Libbus et al. |
| 2015/0257644 | A1 * | 9/2015 | Cao ......................... H04Q 9/00 |
| | | | 600/509 |
| 2015/0374244 | A1 | 12/2015 | Yoo et al. |
| 2016/0287142 | A1 | 10/2016 | Han et al. |
| 2016/0287177 | A1 | 10/2016 | Huppert et al. |
| 2017/0164855 | A1 | 6/2017 | Solosko et al. |
| 2019/0154723 | A1 | 5/2019 | Kacyvenski et al. |

FOREIGN PATENT DOCUMENTS

| | | |
|---|---|---|
| JP | 2016-518881 | 6/2016 |
| KR | 10-0693861 | 3/2007 |
| KR | 10-1408845 | 6/2014 |
| KR | 10-1556739 | 10/2015 |
| KR | 10-2016-0065948 | 6/2016 |
| KR | 10-2016-0088882 | 7/2016 |
| KR | 10-2016-0119612 | 10/2016 |

OTHER PUBLICATIONS

Written Opinion for International Application PCT/KR2019/000906, dated May 7, 2019.
Office Action issued in Korean counterpart application No. 10-2018-0021064 dated Jun. 12, 2019.
Decision of Final Rejection issued in Korean counterpart application No. 10-2018-0021064 dated Dec. 12, 2019.
Office Action issued in Korean counterpart application No. 10-2018-0021064 dated Jan. 8, 2020.
Office Action issued in Korean counterpart application No. 10-2019-0169402 dated Jan. 16, 2020.
Supplementary European Search Report issued in EP Application No. 19758242.2, dated Sep. 8, 2021, 8 pages.

* cited by examiner

ELECTROCARDIOGRAM MEASUREMENT SYSTEM COMPRISING PATCH-TYPE ELECTROCARDIOGRAM MEASUREMENT APPARATUS

CROSS-REFERENCE OF RELATED APPLICATIONS AND PRIORITY

This application is a continuation of PCT/KR2019/000906, filed on Jan. 22, 2019, which claims the benefit of Korean Patent Application No. 10-2018-0021064 filed on Feb. 22, 2018, the disclosures of which are incorporated herein in their entireties by reference.

TECHNICAL FIELD

The present disclosure relates to an electrocardiogram measurement system comprising a patch-type electrocardiogram measurement apparatus, and more particularly, to an electrocardiogram measurement system comprising a patch-type electrocardiogram measurement apparatus capable of being connected to an external device to store electrocardiogram data.

BACKGROUND

Products related to storage of the electrocardiogram (ECG) data known to date are largely divided into products in which data is stored in an embedded memory in a patch-type measurement apparatus itself and products in which data is transmitted to a smartphone through Bluetooth Low Energy (BLE) communication and stored in a memory in the smartphone, while an ECG signal is output in real time onto the screen of the smartphone.

For a patch-type ECG measurement apparatus using an embedded memory, it is necessary to secure a memory space, which is disadvantageous in that miniaturization of the patch-type ECG measurement apparatus and memory reuse are not allowed. Furthermore, a patch-type ECG measurement apparatus that stores data in the memory of the smartphone has a limitation in that the smartphone must always be carried and connected.

In the prior art, exemplified is an electrode patch for ECG measurement and an ECG measurement device using same disclosed in Korean Application Publication No. 10-2012-0084950 (published on Jul. 31, 2012).

SUMMARY

Provided is an electrocardiogram (ECG) measurement system comprising a patch-type ECG measurement apparatus in which ECG data is to be stored. Accordingly, it is possible to miniaturize the patch-type ECG measurement apparatus, and is not necessary to always carry a smartphone.

According to an aspect of the present disclosure, an electrocardiogram measurement system includes: a patch-type electrocardiogram measurement apparatus; a first device connected to the electrocardiogram measurement apparatus by means of a first communication method and configured to store the electrocardiogram data measured by the electrocardiogram measurement apparatus; and a second device connected to the electrocardiogram measurement apparatus by means of the first communication method and configured to store the electrocardiogram data measured by the electrocardiogram measurement apparatus.

Furthermore, the electrocardiogram data measured by the electrocardiogram measurement apparatus may include measured time information. A first time period in which the first device stores the electrocardiogram data measured by the electrocardiogram measurement apparatus, and a second time period in which the second device stores the electrocardiogram data measured by the electrocardiogram measurement apparatus may be at least partially at different times.

Specifically, the first device may receive and store the electrocardiogram data stored in the second device that has been measured by the electrocardiogram measurement apparatus. the first device may combine the electrocardiogram data stored in the first device and the electrocardiogram data received from the second device using the measured time information included in each piece of the electrocardiogram data.

In addition, when the second device is connected and the first device displays the electrocardiogram data through an application program installed in the first device, the first device may combine and display the electrocardiogram data stored in the first device and the electrocardiogram data received from the second device using the measured time information included in each piece of the electrocardiogram data.

Furthermore, in a state where the second device is connected with the electrocardiogram measurement apparatus by means of the first communication method, the first device may be characterized by instructing the second device to release the connection from the electrocardiogram measurement apparatus when the first device is in a state of being able to be connected with the electrocardiogram apparatus.

In a state where the second device is able to be connected with the electrocardiogram measurement apparatus by means of the first communication method, the first device may be characterized by instructing the second device to be connected with the electrocardiogram measurement apparatus.

In addition, when there is no external device that is able to receive the electrocardiogram data measured in the electrocardiogram measurement apparatus, the electrocardiogram measurement apparatus may generate a warning signal. Furthermore, when the first device is unable to receive the electrocardiogram data measured in the electrocardiogram measurement apparatus, and the second device is also unable to receive the electrocardiogram data measured in the electrocardiogram measurement apparatus, the first device may generate a warning signal.

According to the electrocardiogram (ECG) measurement system comprising the patch-type ECG measurement apparatus of the present disclosure, a device in which ECG data is to be stored may be selectively used, and thus, it is possible to miniaturize the patch-type ECG measurement apparatus and is not necessary to always carry the smartphone and keep in connection.

DETAILED DESCRIPTION

Hereinafter, an electrocardiogram (ECG) measurement system comprising a patch-type ECG measurement apparatus according to an embodiment of the present disclosure will be described in detail with reference to the accompanying drawings.

The following embodiments of the present disclosure are intended to embody the present disclosure, but not to limit or restrict the scope of the present disclosure. From the detailed description and embodiments of the present disclosure, all techniques easily conceivable by those skilled in the art to which the present disclosure pertains can be easily interpreted as belonging to the scope of the present disclosure.

Figure 1:
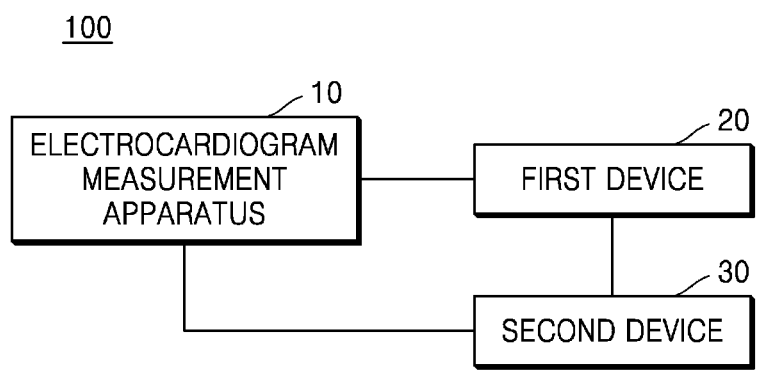
FIG. 1 is a configuration diagram of an electrocardiogram (ECG) measurement system comprising a patch-type ECG measurement apparatus according to an embodiment of the present disclosure.

First, FIG. 1 is a configuration diagram of an ECG measurement system 100 comprising a patch-type ECG measurement apparatus according to an embodiment of the present disclosure.

As may be known from FIG. 1, the ECG measurement system 100 according to the embodiment of the present disclosure includes an ECG measurement apparatus 10, a first device 20, and a second device 30.

Figure 2:
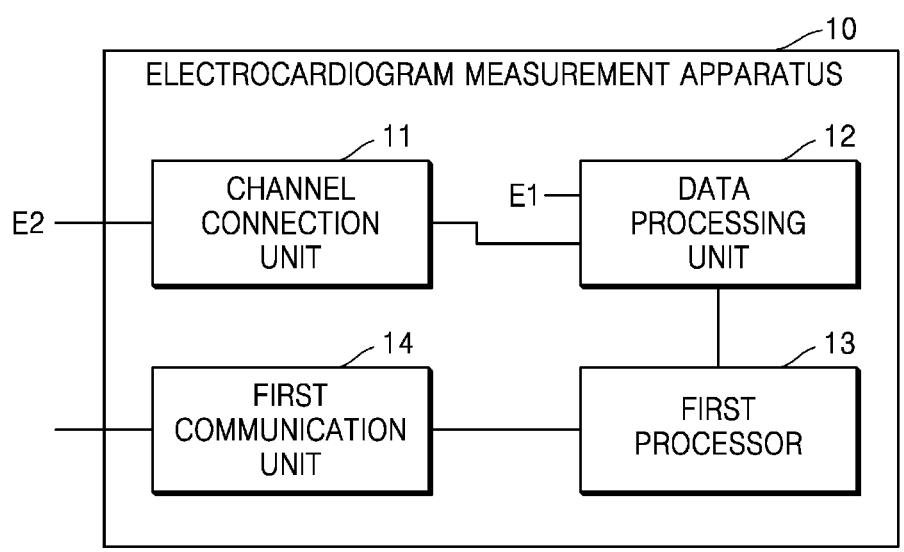
FIG. 2 is a configuration diagram of an ECG measurement apparatus according to an embodiment of the present disclosure.

FIG. 2 is a configuration diagram of the ECG measurement apparatus 10 according to an embodiment of the present disclosure.

As may be known from FIG. 2, the ECG measurement apparatus 10 may be configured by including a plurality of electrodes E1, a channel connection unit 11, a data processing unit 12, a first processor 13, and a first communication unit 14.

The ECG measurement apparatus 10 has the shape of a patch type, and is attached to a human body to be able to measure ECG data of one or more channels by means of the plurality of electrodes E1. In addition, the number of ECG measurement channels of the ECG measurement apparatus 10 is possibly extended by receiving the ECG measurement data of the one or more channels, which is measured by means of the external electrodes E2, through the channel connection unit 11. As the channel connection unit 11, an input terminal form may be exemplified which enables the measurement data from the external electrodes E2 to be used as an input of the data processing unit 12.

The ECG data measured by means of the electrodes E1 of the ECG measurement apparatus 10 itself or the external electrodes E2 is amplified by the data processing unit 12 and then converted into a digital signal. To this end, the data processing unit 12 preferably includes an amplifier and an analog-to-digital converter.

Furthermore, the ECG data output from the data processing unit 12 is inserted with time information at which the ECG data has been measured by the first processor 12, namely, a time-stamp, and then transmitted to an external device by means of a first communication method through the first communication unit 14. Specifically, the first communication method may be exemplified by a Bluetooth low energy (BLE) communication. The ECG measurement apparatus 10 may transmit the ECG data to the external device and receive data from the external device through the first communication unit 14. Here, for convenience, the description is provided only with the ECG data, but it is natural to include a necessary control signal together with the data.

Figure 3:
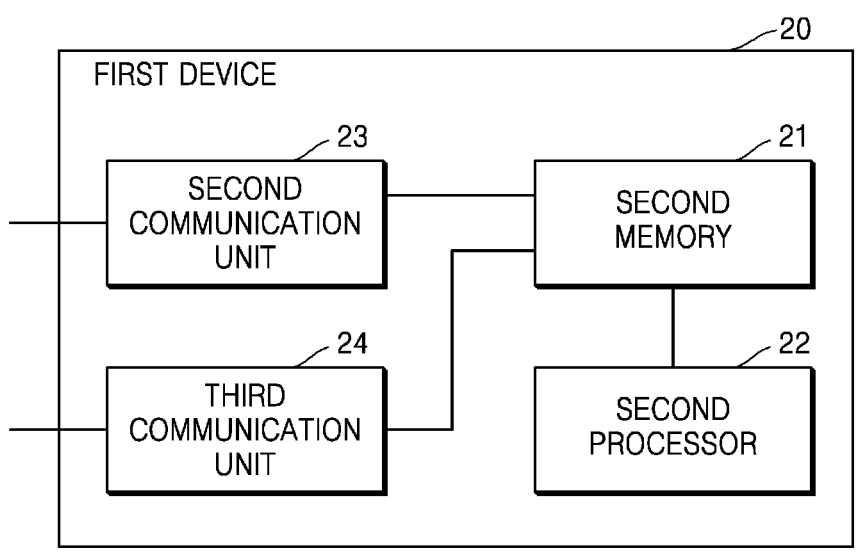
FIG. 3 is a configuration diagram of a first device according to an embodiment of the present disclosure.

FIG. 3 is a configuration diagram of the first device 20 according to an embodiment of the present disclosure.

As may be known from FIG. 3, the first device 20 may be configured by including a second memory 21, a second processor 22, a second communication unit 23, and a third communication unit 24. As an example, the first device 20 may be implemented using a mobile terminal, which can be a smartphone, a tablet PC, or the like.

The second memory 21 may store the ECG data measured by the ECG measurement apparatus 10. The first device 20 is installed with an application program, and thus the second processor 22 may execute the application program. When the application program is executed by the second processor 22, the ECG data stored in the second memory 21 may be processed to be displayed on a screen of the first device 20.

The second communication unit 23 receives the ECG data from the ECG measurement apparatus 10 by means of the first communication method. The first communication method may be exemplified by the BLE communication. The ECG data received by the second communication unit 23 is stored in the second memory 21. The ECG data received from the ECG measurement apparatus 10 is characterized by being inserted with the time information at which the ECG data has been measured, namely, the time-stamp.

The third communication unit 24 enables transmission and reception of data with the second device by means of a wireless or wired communication method other than the first communication method. The third communication unit (24) may use a WiFi communication as another example. Naturally, the second device 30 and the first device 20 may be directly connected through a USB terminal of the first device 20 and then data is input from or output to the second device 30. The ECG data input from the second device 30 through the third communication unit 24 or a direct connection is stored in the second memory 21.

Figure 4:
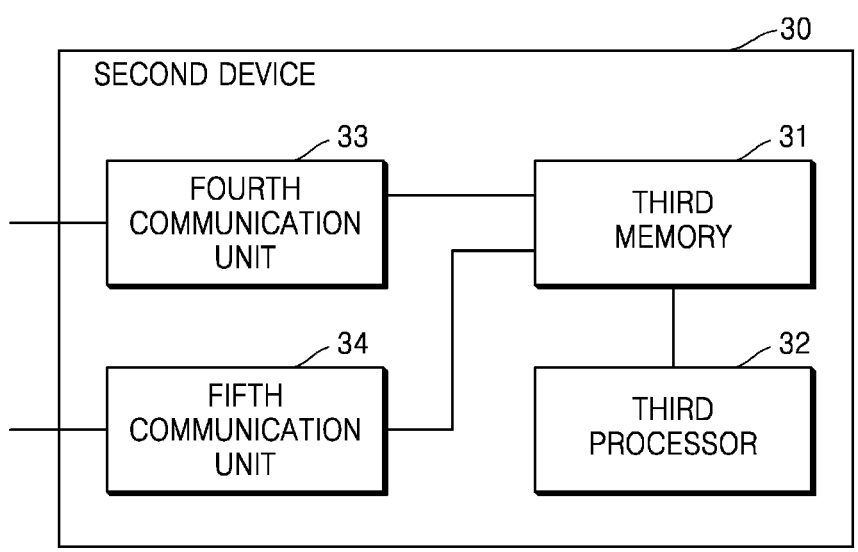
FIG. 4 is a configuration diagram of a second device according to an embodiment of the present disclosure.

FIG. 4 is a configuration diagram of the second device 30 according to an embodiment of the present disclosure.

As may be known from FIG. 4, the second device 30 may be configured by including a third memory 31, a third processor 32, a fourth communication unit 33, and a fifth communication unit 34. As an example, the second device 30 is preferably implemented with a device miniaturized by mounting a communication function onto a dongle memory.

The third memory 31 may store the ECG data measured by the ECG measurement apparatus 10. The third processor 32 may execute processing or the like for the ECG data.

The fourth communication unit 33 receives the ECG data from the ECG measurement apparatus 10 by means of the first communication method. The first communication method may be exemplified by the BLE communication. The ECG data received by the fourth communication unit 33 is stored in the third memory 31. The ECG data received from the ECG measurement apparatus 10 is characterized by being inserted with the time information at which the ECG data has been measured, namely, the time-stamp.

The fifth communication unit 34 enables transmission and reception of data with the first device 20 by means of a wireless communication method other than the first communication method. The fifth communication unit (34) may use a WiFi communication as an example. Naturally, the second device 30 and the first device 20 may be directly connected through a USB terminal of the first device 20 and thus data transmission and reception with the second device 30 become possible.

Hereinafter, a detailed description will be provided about a method for storing the ECG data, which has been measured by the ECG measurement apparatus 10, in the first device 20 and the second device 30.

The first device 20 preferably operates as a master device that may transmit a command to the second device 30 to control the operation of the second device 30. In other words, the second device 30 is characterized by operating as a slave device. Accordingly, the first device 20 may not only receive connection status information about the second device 30 with another device, but also transmit a command for connecting the second device 30 with the other device or a command for releasing the connection of the second device 30 from the other device. Here, the other device may be the ECG measurement apparatus 10.

When the first device 20 is connected to the ECG measurement apparatus 10 by means of the first communication method, the ECG data measured by the ECG measurement apparatus 10 is stored in the first device 20.

In addition, when the connection of the first device 20 with the ECG measurement apparatus 10 through the first communication method is released, the second device 30 may be automatically connected to the ECG measurement apparatus 10 when the second device 30 is present around the ECG measurement apparatus 10. Accordingly, the ECG data measured by the ECG measurement apparatus 10 is stored in the second device 30.

In other words, a time period in which the first device 20 stores the ECG data measured by the ECG measurement apparatus 10, and a time period in which the second device 30 stores the ECG data measured by the ECG measurement apparatus 10 are different from each other, and thus the time periods do not overlap. In other words, the time period in which the first device 20 stores the ECG data measured by the ECG measurement apparatus 10, and the time period in which the second device 30 stores the ECG data measured by the ECG measurement apparatus 10 are characterized by being at different times. This is caused by the characteristics of the BLE communication in which only one device may be connected to one communication module. Furthermore, even when a communication in which many devices are connected at the same time is used, namely, even when the first device 20 and the second device 30 simultaneously store the ECG data, overlapping ECG data may be discerned by means of the time information, namely, the time-stamp. To sum up, the time period in which the first device 20 stores the ECG data measured by the ECG measurement apparatus 10, and the time period in which the second device 30 stores the ECG data measured by the ECG measurement apparatus 10 may be at least partially at different times.

The first device 20 may receive and store the ECG data that has been measured by the ECG measurement apparatus 10 and stored in the second device 30. The first device 20 and the second device 20 may be exemplarily connected by means of a wireless communication method other than the first communication method, or a direct connection.

Figure 5:
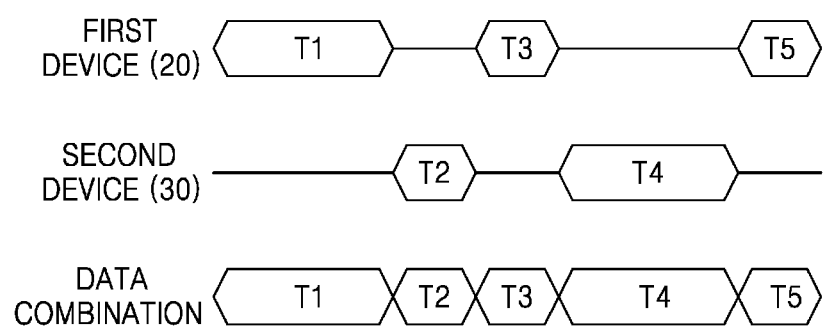
FIG. 5 is an illustration of a combination of ECG data in the first device.

FIG. 5 is an illustration of a combination of the ECG data in the first device 20. Here, for convenience of explanation, the ECG data is shown not overlapping, but it is natural that the ECG data stored in the first device 20 and the ECG data stored in the second device 20 at least partially overlap. This overlapping portion may be discerned by means of the time-stamp that is the characteristics of the present disclosure.

The first device 20 combines the ECG data, which has been measured by the ECG measurement apparatus 10 and stored in the first device 20, and the ECG data, which has been measured by the ECG measurement apparatus 10 and stored in the second device 30, using the measured time information included in each piece of the ECG data, and then newly store the combined ECG data in the first device 20.

In detail, when the second device 30 is connected and the ECG data is processed (displayed as an example) through an application program installed in the first device 20, the first device 20 is characterized by combining the ECG data, which has been measured by the ECG measurement apparatus 10 and stored in the first device 20, and the ECG data, which has been measured by the ECG measurement apparatus 10 and stored in the second device 30, using the measured time information included in each piece of the ECG data, and displaying the combined ECG data on the screen of the first device 20.

The first device 20 may select one of the first device 20 or the second device 30 and allow the ECG data measured by the ECG measurement apparatus 10 to be stored therein. Hereinafter, a method in which the first device 20 selects one of the first device 20 or the second device 30 will be described.

In a state where the second device 30 is connected with the ECG measurement apparatus 10 by means of the first communication method, when the first device 20 is in a state of being able to be connected to the ECG measurement apparatus 10 by means of the first communication method, the first device 20 instructs the second device 30 to release the connection from the ECG measurement apparatus 10. Accordingly, the connection between the second device 30 and the ECG measurement apparatus 10 is released, the first device 20 is connected with the ECG measurement apparatus 10, and thus the ECG data measured in the ECG measurement apparatus 10 is stored in the first device 20.

In addition, when the second device 30 is in a state of being able to be connected to the ECG measurement apparatus 10 by means of the first communication method, the first device 20 may instruct the second device 30 to be connected with the ECG measurement apparatus 10. As an example, in a state where the first device 20 is connected with the ECG measurement apparatus 10 by means of the first communication method, when the first device 20 intends to stop the storage of the ECG data, the first device 20 may release the connection of itself from the ECG measurement apparatus 10, and allow the second device 20 to be connected with the ECG measurement apparatus 10. However, when the first device 20 releases the connection of itself with the ECG measurement apparatus 10, the second device 30 may be automatically connected with the ECG measurement apparatus 10 when the second device 30 is present around the ECG measurement apparatus 10.

When there is not any external device including the first device 20 or the second device 30 that may receive the ECG data measured by the ECG measurement apparatus 10, the ECG measurement apparatus 10 generates a warning signal to inform a user of a situation in which the ECG data is not possibly stored.

Furthermore, when the first device 20 is not able to receive the ECG data measured by the ECG measurement apparatus 10, and the second device 20 is not also able to receive the ECG data measured by the ECG measurement apparatus 10, the first device 20 may generate a warning signal.

In other words, the warning signal in the present disclosure may be generated by the ECG measurement apparatus 10 and/or the first device 20.

As the foregoing, according to the ECG measurement system 100 comprising a patch-type ECG measurement apparatus 10 of the present disclosure, any one of the first device 20 and the second device 30 may be selectively used as a device in which the ECG data is to be stored. Accordingly the patch-type ECG measurement apparatus 10 does not require a separate and embedded large-capacity memory, and thus may be miniaturized.

In addition, according to the ECG measurement system 100 comprising the patch-type ECG measurement apparatus 10 of the present disclosure, it is not necessary to always carry the first device 20 of a large size like a smartphone, and the ECG data may be stored in the second device 30 of a small dongle type. Furthermore, according to the ECG measurement system 100 comprising the patch-type ECG measurement apparatus 10 of the present disclosure, pieces of the ECG data stored in different devices at different times are combined to one piece of data using the measured time information and thus the entire ECG data may be constructed, which increases the convenience of use.

What is claimed is:

1. An electrocardiogram measurement system comprising:
    an electrocardiogram measurement apparatus configured to measure an electrocardiogram data by means of one or more electrodes, amplify the electrocardiogram data, convert digitally the electrocardiogram data, and transmit the amplified and digitized electrocardiogram data to a first device or transmit the electrocardiogram data to a second device through a first communication unit;
    the first device comprising a first processor, a second communication unit, a third communication unit and a first memory, the first device configured to:
        receive first electrocardiogram data and measured time information from the electrocardiogram measurement apparatus via the second communication unit,
        store the first electrocardiogram data measured by the electrocardiogram measurement apparatus in the first memory for a first time period,
        transmit a command for making a connection with the electrocardiogram measurement apparatus to the second device via the third communication unit, and
        release a connection from the electrocardiogram measurement apparatus after the transmitting the command for making the connection to the second device; and
    the second device comprising a second processor, a fourth communication unit, a fifth communication unit and a second memory, the second device communicates with the first device through a wireless communication at a request of the first device, the second device configured to:
        receive second electrocardiogram data and measured time information from the electrocardiogram measurement apparatus via the fourth communication unit in response to the command for making the connection with the electrocardiogram measurement apparatus from the first device via the fifth communication unit, and
        store the second electrocardiogram data measured by the electrocardiogram measurement apparatus for a second time period in the second memory, wherein:
    the electrocardiogram measurement apparatus transmits the second electrocardiogram data to the second device via the first communication unit while the electrocardiogram measurement apparatus is not communicating with the first device;
    the first time period is a time period during which the first device communicates with the electrocardiogram measurement apparatus; and
    the second time period is a time period during which the second device communicates with the electrocardiogram measurement apparatus and the first device does not communicate with the electrocardiogram measurement apparatus.

2. The electrocardiogram measurement system of claim 1, wherein the first device is further configured to:
    receive the second electrocardiogram data from the second device via the third communication unit for a third time period,
    store the second electrocardiogram data, and
    generate combined data by combining the first electrocardiogram data and the second electrocardiogram data using the measured time information included in the first and the second electrocardiogram data.

3. The electrocardiogram measurement system of claim 1, wherein the first device is further configured to:
    determine that a connection status information of the second device indicates the connection with the electrocardiogram measurement apparatus;
    transmit a command for releasing the connection to the second device; and
    upon receipt of the connection status information of the second device indicative of the release from the electrocardiogram measurement apparatus, connect with the electrocardiogram measurement apparatus.

4. The electrocardiogram measurement system of claim 2, wherein the first device displays the combined data using an application program.

5. The electrocardiogram measurement system of claim 1, wherein the electrocardiogram measurement apparatus is configured to generate a warning signal, when there is no external device that is able to receive available electrocardiogram data.

6. The electrocardiogram measurement system of claim 1, wherein the first device is further configured to generate a warning signal to receive a third electrocardiogram data measured in the electrocardiogram measurement apparatus, when both the first device and the second device are disconnected.

7. A method of operating an electrocardiogram measuring system comprising an electrocardiogram measurement apparatus, a first device capable of communicating with the electrocardiogram measurement apparatus, and a second device capable of communicating with the electrocardiogram measurement apparatus, the method comprising:
    measuring, by the electrocardiogram measurement apparatus, electrocardiogram data by means of one or more electrodes, amplifying the electrocardiogram data, converting digitally the electrocardiogram data, and transmitting the amplified and digitized electrocardiogram data to the first device or transmit the electrocardiogram data to the second device through a first communication unit of the electrocardiogram measurement apparatus;
    receiving, by the first device, first electrocardiogram data and measured time information from the electrocardiogram measurement apparatus for a first time period, and storing the first electrocardiogram data in a first memory of the first device;

transmitting, by the first device, a command for making a connection with the electrocardiogram measurement apparatus to the second device through a wireless communication method;

releasing, by the first device, a connection with the electrocardiogram measurement apparatus after the transmitting the command for making the connection to the second device;

connecting, by the second device, to the electrocardiogram measurement apparatus in response to the command for making the connection with the electrocardiogram measurement apparatus from the first device through the wireless communication method;

receiving, by the second device, a second electrocardiogram data and measured time information from the electrocardiogram measurement apparatus for a second time period, and storing the second electrocardiogram data in a second memory of the second device;

transmitting, by the electrocardiogram measurement apparatus, the second electrocardiogram data to the second device while the electrocardiogram measurement apparatus is not communicating with the first device; and transmitting, by the electrocardiogram measurement apparatus, the electrocardiogram data to the first device or the second device connected; and wherein the first time period is a time period during which the electrocardiogram measurement apparatus communicates with the first device, the second time period is a time period during which the electrocardiogram measurement apparatus communicates with the second device and does not communicate with the first device, and the second device communicates with the first device through the wireless communication method at a request of the first device.

8. The method of claim 7 further comprising:
receiving, by the first device, the second electrocardiogram data from the second device via a third communication unit for a third time period, storing the second electrocardiogram data, and generating combined data by combining the first electrocardiogram data and the second electrocardiogram data using the measured time information included in the first and the second electrocardiogram data.

9. The method of claim 7, further comprising:
determining, by the first device, that connection status information of the second device indicates the connection with the electrocardiogram measurement apparatus;

transmitting, by the first device, a command for releasing the connection with the electrocardiogram measurement apparatus to the second device; and connecting, by the first device, with the electrocardiogram measurement apparatus upon receipt of the connection status information of the second device indicative of a release from the electrocardiogram measurement apparatus.

10. The method of claim 8, further comprising:
displaying, by the first device, the combined data using an application program.

11. The method of claim 7, wherein the electrocardiogram measurement apparatus is configured to generate a warning signal, when there is no external device that is able to receive available electrocardiogram data.

* * * * *